US010258471B2

(12) United States Patent
Lutter et al.

(10) Patent No.: US 10,258,471 B2
(45) Date of Patent: Apr. 16, 2019

(54) CATHETER

(75) Inventors: Georg Lutter, Kiel (DE); Lucian Lozonschi, Madison, WI (US)

(73) Assignee: VDYNE, LLC, Dallas, TX (US)

( * ) Notice: Subject to any disclaimer, the term of this patent is extended or adjusted under 35 U.S.C. 154(b) by 60 days.

(21) Appl. No.: 13/148,193

(22) PCT Filed: Feb. 11, 2009

(86) PCT No.: PCT/DE2009/000176
§ 371 (c)(1),
(2), (4) Date: Sep. 28, 2011

(87) PCT Pub. No.: WO2010/091653
PCT Pub. Date: Aug. 19, 2010

(65) Prior Publication Data
US 2012/0010694 A1  Jan. 12, 2012

(51) Int. Cl.
*A61F 2/24* (2006.01)
*A61M 25/01* (2006.01)

(52) U.S. Cl.
CPC ........... *A61F 2/2445* (2013.01); *A61M 25/01* (2013.01)

(58) Field of Classification Search
CPC .... A61F 2/2445; A61F 2/2409; A61F 2/2442; A61F 2/2418; A61F 2/24; A61F 2/2427; A61M 25/0074
USPC ............ 604/167.02, 167.06; 623/1.12, 1.15, 623/1.16, 1.28; 600/114, 115, 116; 606/192, 194
See application file for complete search history.

(56) References Cited

U.S. PATENT DOCUMENTS 3,657,744 A  4/1972 Ersek
5,411,552 A  5/1995 Andersen
5,607,462 A * 3/1997 Imran ........................... 607/122
(Continued)

FOREIGN PATENT DOCUMENTS

DE  10 2007 043831    4/2009
EP    1 264 582 A2    12/2002
(Continued)

OTHER PUBLICATIONS

Arita, M., et al. "Static Analysis of Annuloplasty Rings Sutured on an Annulus Model of the Mitral Valve: Comparison between the Duran Ring and the Carpentier Classic Ring". J Artif Organs (2004) 7: 30-36. (Year: 2004).*

(Continued)

*Primary Examiner* — Brian E Pellegrino
*Assistant Examiner* — Rebecca Lynee Zimmerman
(74) *Attorney, Agent, or Firm* — Juneau & Mitchell; Todd L. Juneau

(57) ABSTRACT

The invention relates to a catheter (10*a*), comprising a flexible catheter body (10*a*) forming at least two hollow spaces (90, 100/110) along the longitudinal extension thereof, characterized in that the catheter body (10*a*) comprises at least two consecutively arranged sections (20) having sheaths (60) that are arranged between the sections (20) and seal the hollow spaces (90, 100/110) at least in some sections, wherein the one hollow space (90) is designed so it communicates with at least one opening (70) penetrating the catheter wall in each section (20), and the other hollow space (100/110) is equipped to introduce an element (40/50) that brings about a longitudinal change of at least one of the sections (20).

11 Claims, 3 Drawing Sheets

(56) References Cited

U.S. PATENT DOCUMENTS

| | | | |
|---|---|---|---|
| 5,662,587 A * | 9/1997 | Grundfest | A61B 1/00082 |
| | | | 600/114 |
| 5,697,905 A | 12/1997 | Ambrosio | |
| 5,855,601 A | 1/1999 | Bessler | |
| 6,168,614 B1 * | 1/2001 | Andersen | A61F 2/2418 |
| | | | 623/1.26 |
| 6,458,153 B1 * | 10/2002 | Bailey | A61F 2/2418 |
| | | | 623/1.24 |
| 7,931,630 B2 * | 4/2011 | Nishtala et al. | 604/318 |
| 8,152,821 B2 * | 4/2012 | Gambale et al. | 606/139 |
| 2002/0116054 A1 * | 8/2002 | Lundell et al. | 623/2.1 |
| 2002/0138138 A1 | 9/2002 | Yang | |
| 2005/0113798 A1 * | 5/2005 | Slater et al. | 604/508 |
| 2006/0025784 A1 | 2/2006 | Starksen et al. | |
| 2007/0233239 A1 | 10/2007 | Navia et al. | |
| 2008/0200980 A1 * | 8/2008 | Robin | A61F 2/2418 |
| | | | 623/2.11 |
| 2009/0224529 A1 * | 9/2009 | Gill | 285/23 |

FOREIGN PATENT DOCUMENTS

| | | |
|---|---|---|
| EP | 2 055 266 A2 | 5/2009 |
| EP | 2 055 266 B1 | 5/2009 |
| FR | 2815844 | 5/2002 |
| NL | 1 017 275 | 8/2002 |
| WO | WO 00/44313 | 8/2000 |
| WO | WO 01/56512 | 8/2001 |
| WO | WO 01/61289 A1 | 8/2001 |
| WO | WO 02/28321 | 4/2002 |
| WO | WO 02/076348 A1 | 10/2002 |

OTHER PUBLICATIONS

International Search Report and Written Opinion from corresponding International Patent Application PCT/US2012/050579, dated Feb. 26, 2013.

U.S. Appl. No. 09/975,750 (U.S. Pat. No. 6,893,460), filed Oct. 11, 2001, Spenser.

Shape Memory Alloys, ttp://webdocs.cs.ualberta.ca/~database; Nov. 14, 2012, pp. 1-3.

Gray, *Gray's Anatomy of the Body*, 1974, pp. ?(1-7), 474-479, 497-498.

Reul, et al., "The Geometry of the Aortic Root in Health, at Valve Disease and After Valve Replacement," *Biomechanics*, vol. 23, No. 2, 1990, pp. 181-191.

Choo, et al., "Aortic Root Geometry: Pattern of Differences Between Leaflets and Sinuses of Valsava," *ICR Publisher*, 1999.

Jin, et al., "Aortic Root Geometry and Stentless Porcine Valve Competence," *Seminars in Thoracic and Cardiovascular Surger*, vol. 11, No. 4, Suppl. 1, Oct. 1999, pp. 145-150.

Webb, et al., "Percutaneous Aortic Valve Implantation Retrograde from the Femoral Artery," *American Heart Association, Inc.*, 2006; pp. 841-850.

Declaration of Malcolm J. R. Dalrymple-Hay, Nov. 9, 2012, pp. 1-11; with Curriculum Vitae, Oct. 4, 2012.

* cited by examiner

CATHETER

The invention relates to a catheter, having a flexible catheter body which forms at least two hollow cavities along the longitudinal extension thereof. The invention particularly relates to a catheter for the reconstruction of a heart valve, particularly the mitral valve.

Catheters are used in a number of different designs for the purpose of minimally invasive diagnostics and therapy. Catheters typical have one or multiple hollow cavities through which fluid can be drained or introduced, or surgical instruments and transplants can be inserted.

Particularly in cases of heart valve ablation, catheters are used which have hollow cavities that both drain fluid and also receive instruments and enable the insertion of a heart valve stent, the latter replacing a malformed or pathologically altered heart valve.

By way of example, in cases of diseases of the mitral valve, physicians attempt to preserve the original heart valve to the greatest extent possible, despite the dysfunction thereof. This is attempted so that the entire, dynamic mitral valve apparatus need not be destroyed. The tendonous cords which attach to the mitral valve are very important for the function of the ventricle, for example, and should therefore not be detached from the original mitral valve to the greatest extent possible. For the purpose of avoiding an open-heart procedure and the use of a heart-lung machine in high-risk patients, minimally invasive methods, including transapical or percutaneous methods, for example, have been developed for the implantation of a heart valve with the assistance of various different catheter systems.

As such, a heart valve prosthesis which can self-expand is know from DE 195 46 692 C2 and EP 1 469 797 B1, incorporated herein for showing a general illustration of how a valve prosthesis is situated within a stent body, for implantation in the human body via a catheter system having a heart valve and having a stent which is connected to the heart valve and which can both collapse and expand. Such a self-expanding heart valve prosthesis can be guided with assistance from a catheter system through a femoral artery and to the implantation site in the heart, then unfolded. Following the unfolding thereof, the heart valve prosthesis can also be anchored with the assistance of anchoring hooks, in or near the heart in the respective blood vessel. The actual heart valve prosthesis itself is situated in the stent in this case.

An additional device for the attachment and anchoring of heart valve prostheses is disclosed by DE 100 10 074 A1, and is substantially formed from wire-shaped elements which are connected to each other. An improved positioning and angular orientation with respect to the aortic valve can be achieved by means of the stent in EP 1 469 797 B1, which discloses the design of so-called support frames which can be inserted into the aortic recesses, thereby producing a defined separation distance from the aortic valve.

Moreover, it is also possible to discontinue a failed implantation of a heart valve prosthesis, and then draw the valve stent (that is, the valve integrated into a stent) back into the catheter system (or more precisely, the cartridge). In this case, the entire stent is then folded back together and guided back into the catheter opening (cartridge), for the purpose of deploying it again in another position upon better positioning.

However, a much larger problem for the optimal placement of the new heart valve in the stent (and/or valve stent) is that the original, native valve, in the majority of the cases involving the implantation techniques described above, should not be removed. This has the result that the new valve which is pressed into (partially squeezed into) an old deformed valve becomes altered from its original stent shape. This is due to the fact that the site of implantation for the valve stent is characterized by the morphology, the condition, and the properties of the original, native valve (in cases of valve sclerosis or calcification of the native valve).

In addition, perfusion catheters or inflatable devices are also known, which enable the creation of an insulated chamber in smaller or larger (aortic) vessels, for the purpose of valve resection: Special perfusion catheters are used in heart surgery, and are known from the concept of the balloon catheter (DE 195 33 601). For example, U.S. Pat. No. 6,135,981 suggests a perfusion catheter having two inflatable chambers which are arranged neighboring each other in a distal orientation. These form an operation space enclosed by the chambers which is excluded from the circulatory system. For the purpose of improving the positioning of the balloon in the vessel, the surface can be modified (U.S. Pat. No. 5,423,745) in a special manner (with knobs or indentations). A device having two inflatable dilation units arranged along the catheter (see DE 102 17 559) is known for the ablation of diseased heart valves.

However, it would be especially desirable, at least in cases of heart failure, to modify and to reconstruct the valve annulus of the defective heart valve of the patient, along with the associated original valve components, using simple measures in such a manner that the insufficiency of the valve can be addressed, rather than completely, or preferably partially removing a malformed or pathologically altered heart valve.

The problem addressed by the present invention is therefore that of creating a catheter which enables the reconstruction of vessel cross-sections, particularly the reconstruction of a failing heart valve, using simple measures.

The problem is addressed according to the invention by the catheter having the features of claim 1. The dependent claims describe advantageous embodiments of the invention.

The invention is based on the idea of segmentally designing a catheter in such a manner that the flexible catheter can be substantially placed as a ring around a structure being reconstructed, for example a heart valve, and can be attached to the same for a long time. The length of individual segments of the catheter can be modified, such that the anatomy of the vessel/valve can be modified, thereby achieving a modification of the cross-section of the affected vessel, and therefore addressing, for example, a heart valve insufficiency.

Therefore, it is of decisive importance that the native annulus can be contracted by means of the catheter according to the invention at the correct position/in the correct segments of the ring-shaped catheter. In this case, the optimal attachment of the catheter to the tissue is also equally important.

For this purpose, the catheter according to the invention for valve reconstruction has special attachment elements which attach the catheter to the vessel tissue in a flush and fluid-tight manner, similarly to the design suggested in PCT/DE2005/000437. WO 00/74574 A1 is also relevant in this case, and shows an object which can suction onto tissue in a ring-shaped manner. However, these disclosures do not render obvious how this attachment could effect a long-term modification of a vessel cross-section.

In order to enable a long-term and stable reconstruction of the vessel cross-section, which can also be carried out with minimally-invasive techniques, the catheter according to the invention forms a foldable catheter which can be repositioned, which can form itself into a valve ring, which has an especially flexible shape and structure, and which can be attached to the heart valve annulus by means of a suctioning structure. The catheter is inserted into a heart chamber, either percutaneously or transapically by means of a catheter introducer or through a large vessel adjoining the heart, and then deployed. Its attachment elements are adjusted in such a manner that an optimal attachment results on the one hand, and on the other hand the native annulus configuration can also be reconstructed and optimized by means of the segments in the catheter which is preferably arranged in a ring shape, said segments being designed with different lengths.

The invention is described in greater detail below with reference to preferred embodiments shown in the illustrations, wherein.

Figure 1:
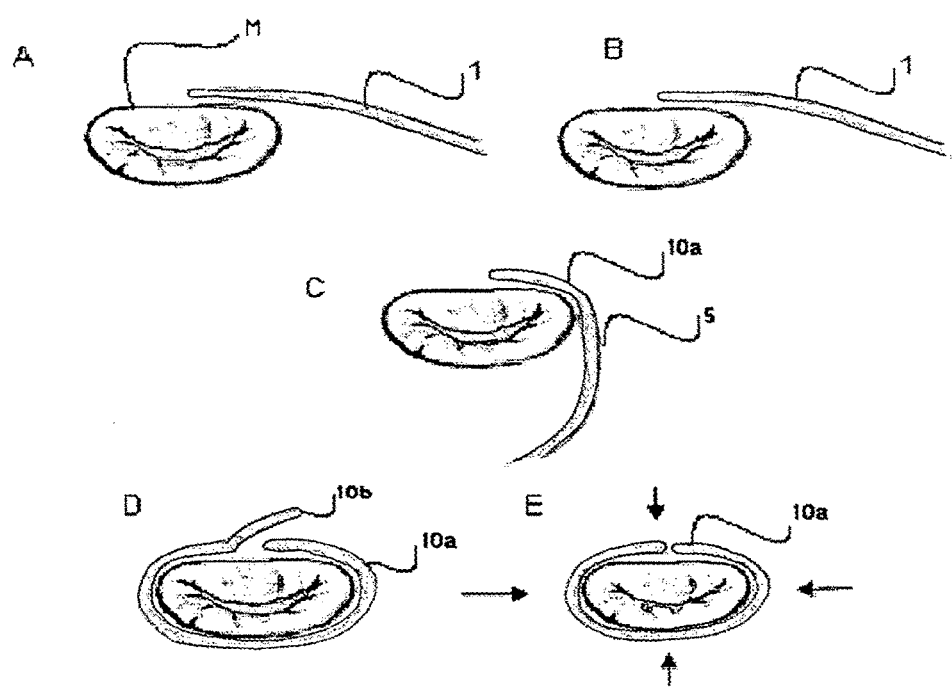
FIG. 1 shows a transversal plane through a human heart, with a top view of the mitral valve with the catheter according to the invention in situ.

FIG. 1 shows, as an exemplary explication of the invention, a transversal plane through a human heart, with a top view of the mitral valve (M), with the catheter 1 according to the invention. In the exterior view, the catheter 1 according to the invention appears similar to a conventional flexible catheter. The catheter 1 according to a preferred embodiment can be formed into a ring conformation by means of Bowden cables (not pictured), and can form a snug fit with the annulus of a diseased, failing mitral valve M. Once the catheter 1 is precisely positioned and successfully attached to the mitral valve M, the individual segments of the catheter can be shortened or lengthened in such a manner that the mitral valve M becomes functional once more (FIG. 1E).

Figure 2:
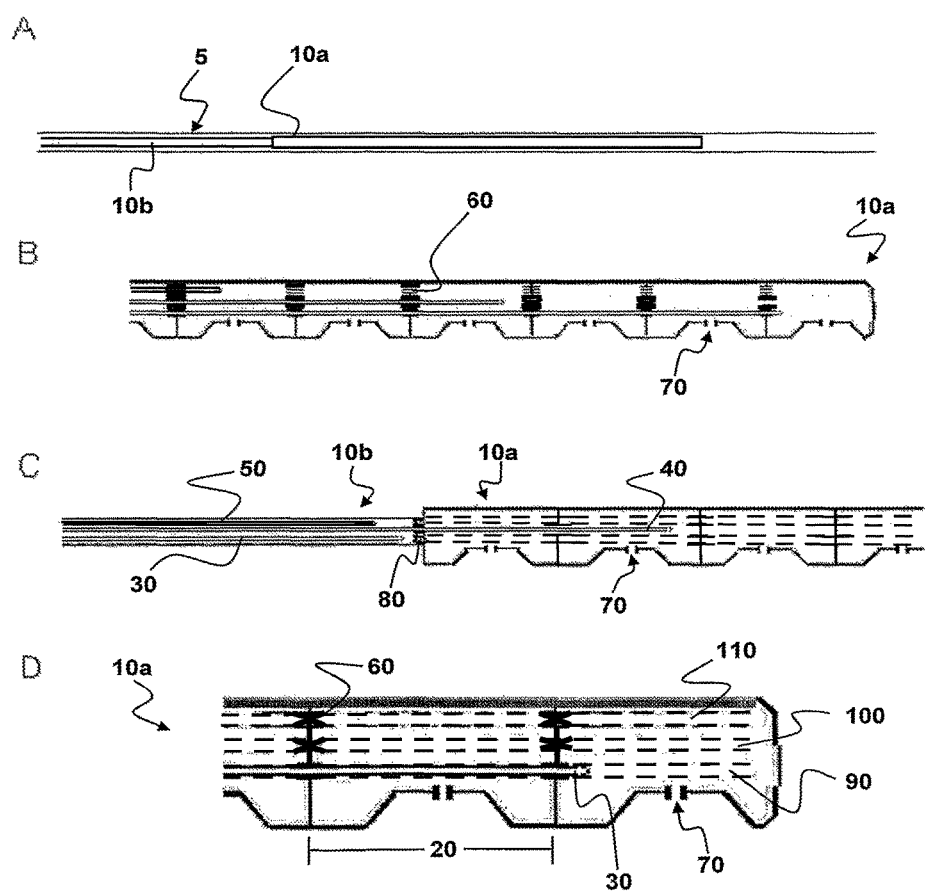
FIG. 2 shows a lateral view of the catheter according to the invention for valve reconstruction.

FIG. 2 shows a longitudinal plane of a particularly preferred embodiment of the catheter according to the invention, in four detailed views:

FIG. 2A shows a particularly preferred embodiment of a catheter system 10 consisting of the catheter 10a according to the invention, a catheter support 10b connected to the catheter 10a in a detachable manner, and a catheter introducer 5 which receives both the catheter 10a and the catheter support 10b. The free end of the catheter introducer is preferably made to be displaceable by means of, for example, Bowden cables, such that the catheter 10a can be pushed out of the catheter introducer 5 in a prespecified direction, and can be adapted to the mitral valve M shown in FIG. 1.

The catheter 10a and the catheter support 10b preferably have a coupling device 80 for connecting the catheter 10a to the catheter support 10b in a detachable manner (FIG. 2C). The coupling device 80 is positioned during the process whereby the catheter support 10b becomes decoupled from the catheter 10a for providing a fluid-tight closure of the hollow cavities situated in the catheter 10a. The coupling device is necessary in order to place the catheter 10a long-term in the patient with a minimally invasive implantation technique.

In FIG. 2B, the catheter 10a is portrayed in a larger view, wherein it can be seen that the catheter 10a is divided into segments by means of fluid locks 60. FIG. 2D further illustrates this:

In the embodiment shown, each segment 20 formed by a fluid lock 60 has three hollow cavities 90, 100, 110 which extend longitudinally with respect to the segment 20. The two hollow cavities 100, 110 illustrated in the example can also be merged into a single hollow cavity 100/110. Fluid locks 60 are arranged in the hollow cavities 90, 100, 110 and divide the hollow cavities 90, 100, 110 into segments. The fluid locks 60 seal the hollow cavities 90, 100, 110 of each segment 20 with respect to each other. However, they can be opened by means of application of a prespecified pressure, for example, such that the hollow cavities 90, 100, 110 of each segment 20 communicate with each other.

However, the fluid locks are preferably made to only open by means of elements 30, 40, 50 (cf. FIG. 2C) provided in the catheter support 10b, wherein said element 30, 40, 50 can be pushed though the hollow cavities 90, 100, 110 through the segments 20 in the direction defined by the longitudinal dimension thereof.

The element 30 in this case preferably serves the purpose of applying suction to the at least one opening 70 of a segment, for the purpose of attaching the catheter 10a to the tissue. Because it may well be difficult to achieve long-term attachment by means of suction, the invention can also include a configuration wherein the element 30 dispenses an adhesive (for example, a fibrin adhesive) via the openings 70, and provides the attachment in this manner.

The elements 40, 50 serve to modify the length of an individual segment 20. The length modification of a single segment 20 can be triggered by the introduction or the removal of a fluid (gas or liquid), for example. If pressure is applied to a segment 20, for example, via a fluid, the segment 20 of the flexible catheter 10a extends, such that the segment 20 sealed off by means of at least one fluid lock 60 lengthens. Conversely, a shortening of a segment 20 can be effected if suction is generated in a segment 20, such that the distance between two fluid locks shortens. In the embodiment, shown in an exemplary illustration, the elements 40, 50 are pushed into the foremost segment 20 following successful attachment to the tissue, the length of the foremost segment 20 is modified, and the segment 20 behind the foremost segment 20 is modified in turn. In this case, the fluid locks 60 are designed to seal off the segments 20 from each other in such a manner that essentially no changes in volume occur when an element 40, 50 has penetrated the segment and then retracted from the same.

In addition, a Bowden cable can be provided in the catheter 10a, and can be used not only for displacing the catheter 10a, but also for shortening the respective segment 20 in an incremental manner.

The respective length modifications of the segments 20, which result in a change in the cross-section of the catheter 10a, the latter being positioned in a ring-shaped configuration, can shorten a particular segment of the valve ring when the catheter 10a is simultaneously attached to the tissue by means of the openings 70 in the respective segments 20. However, the particular segment of the valve ring can also be expanded in order to address the mitral valve insufficiency at hand, for example.

An additional possibility exists (not illustrated) of a configuration wherein only one element 30, 40, 50 is included, and the same can actuate every two or more hollow cavities 90, 100, 110 of the respective sub-unit 20, such that three individual elements 30, 40, 50 need not necessarily be present. This can be implemented in such a manner, for example, that this single element is guided in the coupling 80, such that the element can be inserted into the respective hollow cavity 90, 100, 110 by means of special markings (which are important for the physician).

In the event that it is technically difficult, as indicated above, to produce a vacuum solely by means of the pores 70 of the segments 20 for the purpose of attaching the catheter 10a to the valve annulus, it will be necessary to inject an adhesive (for example glue or fibrin glue) into the respective hollow cavity, such that the volume of the hollow cavity 90, 100, 110 in the respective segment 20 ceases to change and/or can only be modified under controlled conditions. As such, it can be possible to create a long-term vacuum or overpressure using polymer foams—particularly those which release gases during polymerization (e.g., polyurethane foams). The corresponding monomers or auxiliary materials (for example, water for the formation of foam) would then need to be exactly dosed, by way of example in liquid or gaseous form, and would foam up during the curing process and take on the corresponding volume (by means of gaining or losing volume).

Figure 3:
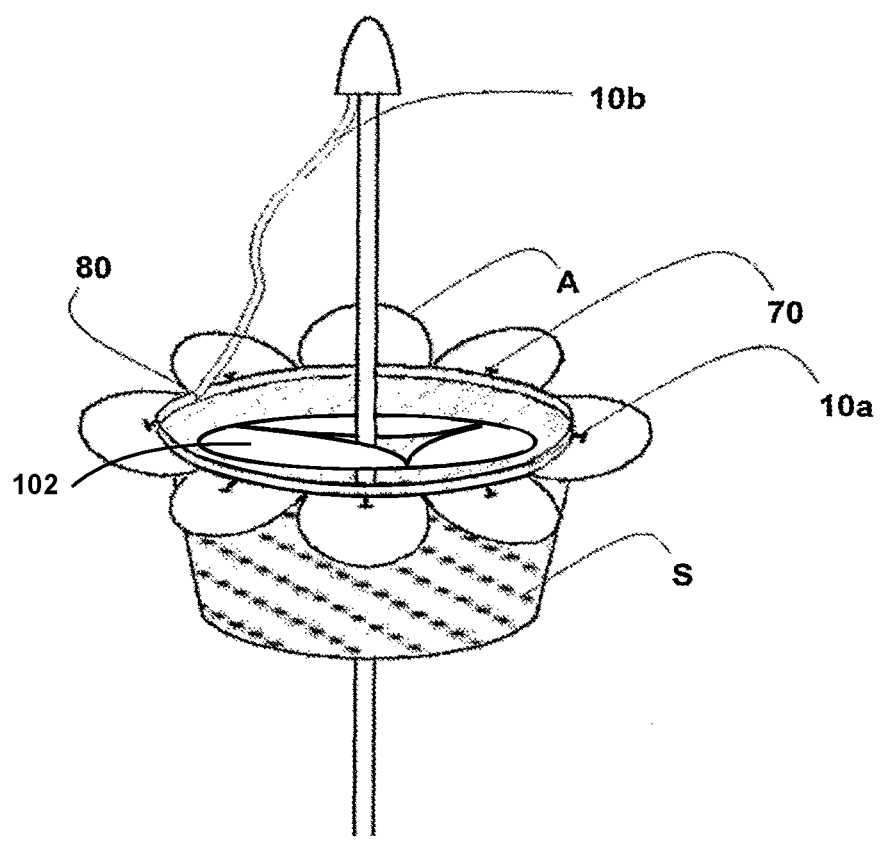
FIG. 3 shows an embodiment of the present invention designed as a valve stent.

According to a further embodiment of the invention, illustrated in FIG. 3, a stent S is designed with a ring-shaped segment 10a which is formed from at least two segments 20 arranged one after the other and having at least two hollow cavities 90, 100/110. The hollow cavities 90, 100/110 are divided into segments by means of fluid locks 60. The hollow cavity 90 is designed to communicate with at least one opening 70 which penetrates the catheter wall in each segment 20. The other hollow cavity 100/110 is designed for the insertion of an element 40/50 which modifies the length of at least one of the segments 20.

With this design, it is possible to adapt the stent S to the anatomical conditions of a vessel, for example the heart, by means of the approach described above for the catheter 10a. In this case, the stent S preferably has additional anchoring means A.

Although the catheter 10a, the catheter system 10, and the stent S according to the invention are only described above with reference to the embodiment of the catheter 10a, the catheter system 10, and the stent S for uses in the human heart, it is also understood that the same can also be used for all types of vessels, such as drain ducts of glands, or in body cavities and other various body segments of differing morphology, for example. In this case, the catheter 10a need not necessarily surround a tissue segment. Rather, it can also adjoin the inner wall of a hollow cavity for the purpose of expanding/contracting the same.

Valve prosthesis 102 is shown within stent S.

The invention claimed is:

1. A system for implantation in a human heart via a catheter system, comprising:
  (i) a generally tubular expandable stent having a prosthetic heart valve connected within the stent;
  (ii) a flexible annular segmented catheter body attached circumferentially around a proximal end of the stent;
  (iii) a plurality of tissue anchors disposed along the length of the catheter body; and
  (iv) a length-adjustment element disposed within the catheter body;
wherein the length-adjustment element comprises a fluid pressure system, wherein generating an increased pressure within a lumen of the catheter body lengthens the catheter body, and generating a decreased pressure shortens the catheter body;
wherein the fluid pressure system comprises:
  a plurality of hollow cavities are disposed within the catheter body along a longitudinal axis;
  a plurality of segments are disposed along the length of the catheter body, and each segment having a closable opening that penetrates a flexible outer wall of the catheter body;
  each hollow cavity within each segment has a closable fluid lock between adjacent segments;
  a slidable element is disposed within each of the plurality of hollow cavities, the slidable element operating to open the closable fluid lock of a segment by sliding longitudinally towards a proximal end of the catheter body, and the slidable element operating to close the closable fluid lock of a segment by sliding longitudinally towards a distal end of the catheter body.

2. The system of claim 1, wherein the length-adjustment element comprises a plurality of segments, wherein extending the length-adjustment element lengthens the catheter body, and withdrawing the length-adjustment element shortens the catheter body.

3. The system of claim 1, wherein the fluid pressure system comprises a plurality of segments disposed along the length of the catheter body, each segment of the plurality of segments having one or more hollow cavities in communication with adjacent segments, and each segment sealed from adjacent segments by one or more fluid locks, each of said fluid locks opened by application of a prespecified pressure.

4. The system of claim 1, wherein the stent is a self-expanding stent.

5. The system of claim 1, wherein the stent comprises tissue anchoring means.

6. The system of claim 1, wherein the stent comprises a plurality of wire-shaped anchoring elements connected to each other.

7. A method of deploying the system of claim 1, comprising the steps:
  (i) delivering the system of claim 1 to a heart chamber via catheter;
  (ii) ejecting the system from the catheter and attaching the catheter body of the system to a native annulus using the tissue anchors; and
  (iii) adjusting the length of the attached catheter body to modify the native annulus shape.

8. The method of claim 7, wherein the (i) step of delivering comprises percutaneous delivering.

9. The method of claim 7, wherein the (i) step of delivering comprises transapical delivering.

10. The method of claim 7, further comprising the step of (iv) attaching the catheter body with adhesive to the native annulus.

11. The method of claim 7, further comprising the step of (iv) detaching the catheter body from a delivery catheter via a detachable coupling element.

* * * * *